United States Patent [19]

Ebara et al.

[11] Patent Number: 5,360,012
[45] Date of Patent: Nov. 1, 1994

[54] BLOOD SAMPLER AND AN AMPLIFIER FOR USE THEREWITH

[75] Inventors: Yukinori Ebara, Suita; Tomoyo Kusakawa, Kusatsu, both of Japan

[73] Assignee: Nissho Corporation, Osaka, Japan

[21] Appl. No.: 31,136

[22] Filed: Mar. 12, 1993

[30] Foreign Application Priority Data

Mar. 24, 1992 [JP] Japan .................. 4-098947
Mar. 24, 1992 [JP] Japan .................. 4-098948

[51] Int. Cl.$^5$ ............................................. A61B 5/00
[52] U.S. Cl. ............................ 128/764; 422/100; 422/102; 422/104; 604/198
[58] Field of Search ............... 422/100, 102, 104; 128/763, 764, 765; 604/198

[56] References Cited

U.S. PATENT DOCUMENTS

| | | | |
|---|---|---|---|
| 3,931,815 | 1/1976 | Takatsuki | 128/2 F |
| 4,150,666 | 4/1979 | Brush | 128/2 F |
| 4,192,320 | 3/1980 | Megahed | 128/764 |
| 4,256,120 | 3/1981 | Finley | 128/764 |
| 4,320,769 | 3/1982 | Eichhorn et al. | 128/763 |
| 4,936,314 | 6/1990 | Kasai et al. | 128/764 |
| 4,976,925 | 12/1990 | Porcher et al. | 422/100 |
| 4,991,601 | 2/1991 | Kasai et al. | 128/763 |

*Primary Examiner*—Nina Bhat
*Attorney, Agent, or Firm*—Adduci, Mastriani, Schaumberg & Schill

[57] ABSTRACT

An adapter 4 fitted in a tube holder 1 is composed of four flexible extensions 23 integral with the forward end of the adapter, and each extension includes a slanted portion 27 and a gripping portion 28 which may have a stopping lug 30 formed on the latter portion. An evacuated tube 3 is closed with a plug 15, which compresses an elastic sheath 12 covering the needle and is pierced by it together with the sheath, when inserted into the adapter 4 for taking a blood sample. The slanted portions 27 are elastically swingable outwardly to render the plug 15 coaxial with the holder 1. The gripping portions 28 are also capable of flexing following the swung slanted portions so that their forward ends are transitionally displaced centrifugally and then restored to their straight position to hold the plug 15 such that even if its outer diameter is considerably smaller than the inner diameter of the holder 1, the sampling needle 2 can penetrate the plug through its central zone and the plug is not "kicked back".

7 Claims, 3 Drawing Sheets

BLOOD SAMPLER AND AN AMPLIFIER FOR USE THEREWITH

BACKGROUND OF THE INVENTION

1. Field of the Invention

The present invention relates to a blood sampler and an adapter for use with the blood sampler.

2. Prior Art

For clinical examinations such as the test of serum or blood cells, blood samples are collected using a blood sampler typically constructed as follows.

The blood sampler comprises in general a tube holder for receiving an evacuated blood sample tube. A sampling needle penetrates a forward end of the tube holder so as to extend forwards, and an elastic sheath fits on a rearward end of the sampling needle so that its fine bore through the rearward end is openably closed. The blood sample tube, which must be evacuated corresponding to the needed quantity of blood sample, is composed of a closed-bottom cylinder and a penetrable plug plugged in the open end of the cylinder.

When the blood sample is to be taken, the sampling needle will be caused to pierce a vein, and then the evacuated tube will be forced into the tube holder so that the penetrable plug presses the elastic sheath in the direction of its axis. As a result, the rearward end of the sampling needle penetrates both the sheath and the plug whereby the needed quantity of blood sample is allowed to flow back into the tube in proportion to its degree of evacuation.

The inner diameter of the tube holders has been designed in general to match the outer diameter of the penetrable plugs plugged in the blood sample tubes. Since the latter diameter is almost the same for the various types of tubes, the conventional tube holders are also of almost the same inner diameter.

It is however a recent tendency that the blood sample tubes of a smaller diameter and thus closed with a smaller plug are preferred.

In a case wherein the conventional tube holder of a normal, or greater diameter is used with the recent smaller tubes, a comparatively large gap will appear between the holder and the tube. Such a large gap will render it difficult for the needle's rearward end to pierce a central portion of the plug. In other words, there is a fear that the needle will erroneously pierce the peripheral zone of the plug.

Generally, the peripheral zone is thicker than the central portion in the axial direction of the plug so that a stronger friction is provided between said zone and the wall of closed-bottom cylinder and the needle can easily pierce the thinner central portion.

If the needle pierces the thick peripheral zone of the plug against a strong resistance, then this resistance which may be stronger than the friction referred to above would cause an unintentional withdrawal of the plug from the cylinder, with the needle being pulled away from the plug.

It is also to be noted that automatic chemical analyzers are now employed widely, which are constructed such that the blood sample tubes are put on a rack and their unremoved plugs are pierced successively by a "testing" needle for sucking the blood samples out of the tubes.

For a speedy sampling of the tested blood samples, the blood sample tubes used with those analyzers must have the plugs less resistant to the testing needle which pierces them.

However, with such a blood sample tube, its elastic sheath compressed by the plug tends to repel the plug when the tube is set in the holder before sampling the tested blood. This repelling force is likely to exceed the plug's friction holding the needle. Thus, the blood sample tube will be pushed backwards so that the "sampling" needle is withdrawn from the plug. This phenomenon is called the "kickback" of the tube, and is a serious problem which must be resolved.

SUMMARY OF THE INVENTION

An object of the present is therefore to provide a kind of adapter which can resolve such a problem when used with a blood sampler.

Another object of the invention is to provide a blood sampler comprising an adapter which is suited to resolve the problems mentioned above.

These objects will be achieved herein in the following manner. Namely, the blood sampler which is to be used with an adapter comprises a tube holder, a sampling needle piercing a forward end of the holder, an elastic sheath fitted on and openably covering a rearward portion and rearward end of the needle, a blood sample tube evacuated and having a plug plugged in an open end of the tube, with the evacuated tube being adapted for insertion in a cylindrical body of the holder when a blood sample is to be taken, wherein the elastic sheath is capable of being compressed in axial direction so that the rearward end of the needle penetrates both the sheath and the plug so as to allow the blood sample to be sucked into the tube, the adapter being interposed between the holder and the evacuated blood sample tube, and comprising: a rearward cylindrical body fittable in the holder; a plurality of forward flexible extensions integral with and forwardly protruding from a forward end of the cylindrical body; the extensions extending axially of said body so as to tightly surround the plug of the inserted blood sample tube; each of the forward flexible extensions comprising a rearward slanted portion and a forward gripping portion integral with and forwardly extending from the slanted portion; the rearward slanted portion being inclined inwardly towards the forward portion and elastically swingable outwardly when caused by the plug of the inserted tube; and the forward gripping portions also capable of flexing following the swung rearward portions so that their forward ends are transitionally displaced centrifugally and then restored to their straight position to hold the plug in place.

It is preferable that each of the gripping portions is formed with a stopping lug which protrudes inwardly from the gripping portion such that the plug of the tube is prevented from backwardly slipping off the gripping portions.

It may also be preferable that three or more flexible extensions are formed at regular angular intervals around the cylindrical body of the adapter, and desirably have a width of 3 mm or less.

The adapter may have its inner surface coated with a silicone agent or the like, especially in a case wherein the extensions are wider than 3 mm.

In operation for taking a blood sample, the adapter has to be set in the tube holder before the sampling needle is caused to pierce a vein. Since in this state the rearward opening of the needle is covered with the elastic sheath, the blood cannot flow back into the tube holder.

Next, the evacuated blood sample tube will be inserted in the adapter, with the plug leading the tube and also with the plug thereby contacting and expanding the slanted portions of the flexible extensions.

The flexible extensions surrounding the tube's plug will guide it while elastically flexing in the radial direction, so that the plug (clicking over the stopping lugs if they are provided) enters a space surrounded by the gripping portions and takes its position accurately coaxial with the adapter and thus coaxial also with the tube holder.

During such a motion of the members, the tube's plug will compress the elastic sheath so that the rear end of the needle does penetrate both the sheath and the plug, thereby permitting a quantity of the blood sample to flow back into the tube, and the quantity corresponding to the reduced internal pressure within the evacuated blood sample tube.

Since the forward gripping portions are transitionally slanted with their forward ends displaced centrifugally when the blood sample tube's plug is inserted, the restoring or righting moment of the flexible extensions will produce a forward component of force which is imparted to the blood sample tube so as to urge it forwards. This component of force will balance the backward force charged by the compressed elastic sheath to the tube, thereby protecting it from being "kicked back". In a case wherein the stopping lugs are formed on the adapter, they prevent the tube from being unintentionally removed from the gripping portions.

As the blood sample flows into the tube, the internal pressure thereof will rise to such a level as disabling any more suction of blood. After a predetermined quantity of blood sample is taken in this way, the tube will be forced backwards out of the adapter so that the rearward portion of the needle removed from the plug will be retracted into the sheath. This sheath which will have recovered its uncompressed state will close the rearward opening of the needle so as not to ooze into the tube holder.

DETAILED DESCRIPTION OF THE PREFERRED EMBODIMENTS

First Embodiment

Figure 1:
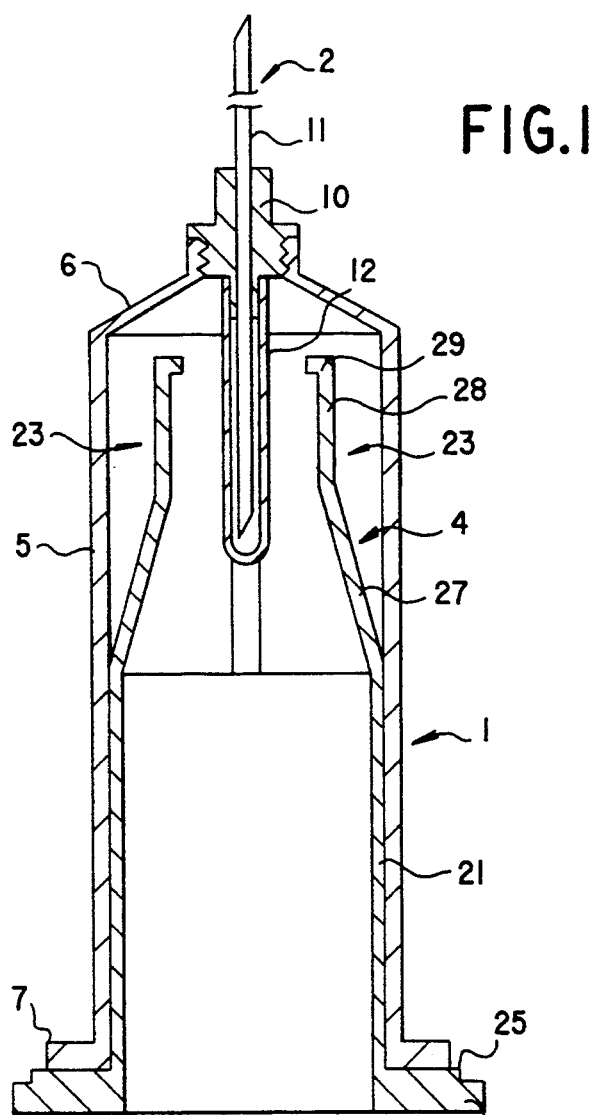
FIG. 1 is a vertical cross section showing a first embodiment of the invention, wherein a tube holder and a type of evacuated blood sample tube are illustrated together with an adapter.
Figure 2:
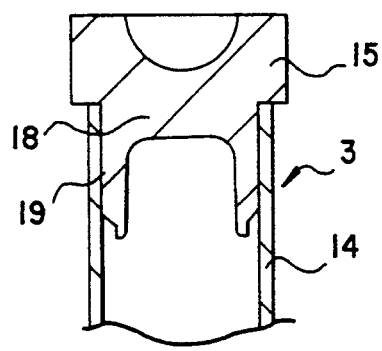
FIG. 2 is another vertical cross section showing the embodiment, wherein the tube holder and a further type of evacuated blood sample tube are illustrated together with the adapter, and wherein the blood sample tube and its plug are of a smaller diameter.
Figure 2:
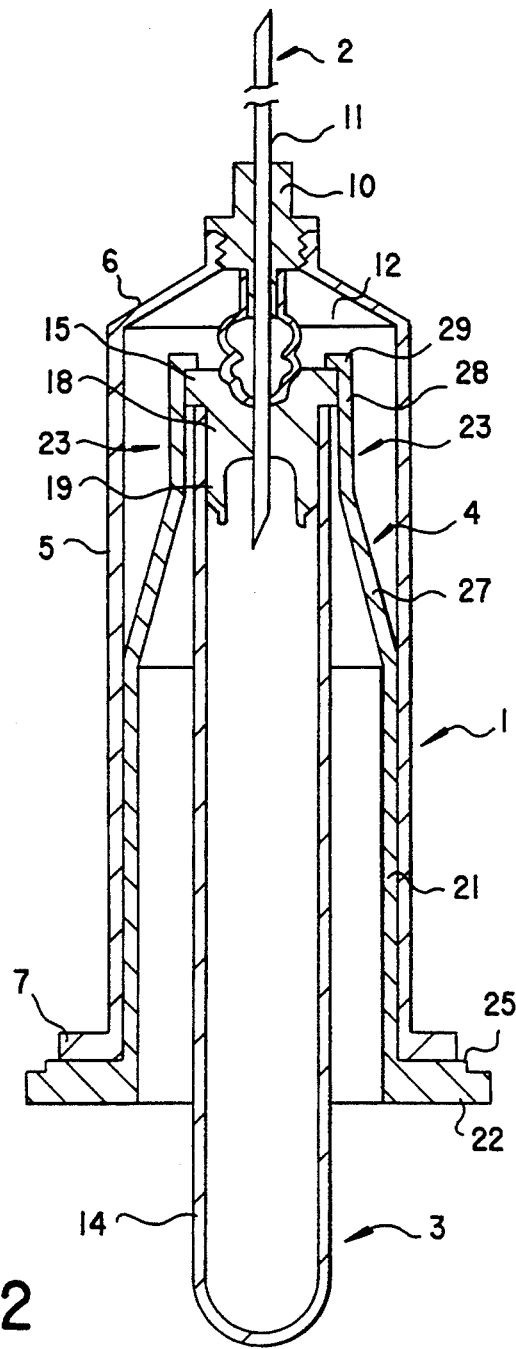
Figure 3:
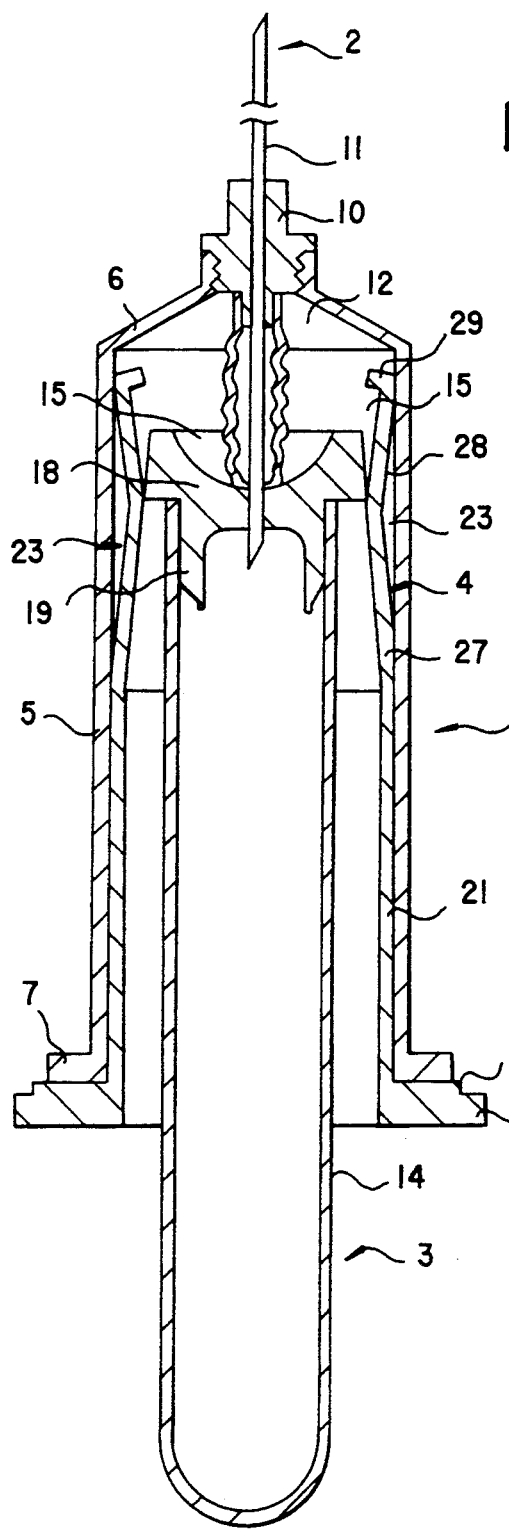
FIG. 3 is still another vertical cross section showing the embodiment, wherein the tube holder and a still further type of evacuated blood sample tube are illustrated together with the adapter, and wherein the blood sample tube has a plug whose central region is extremely thin.
Figure 4:
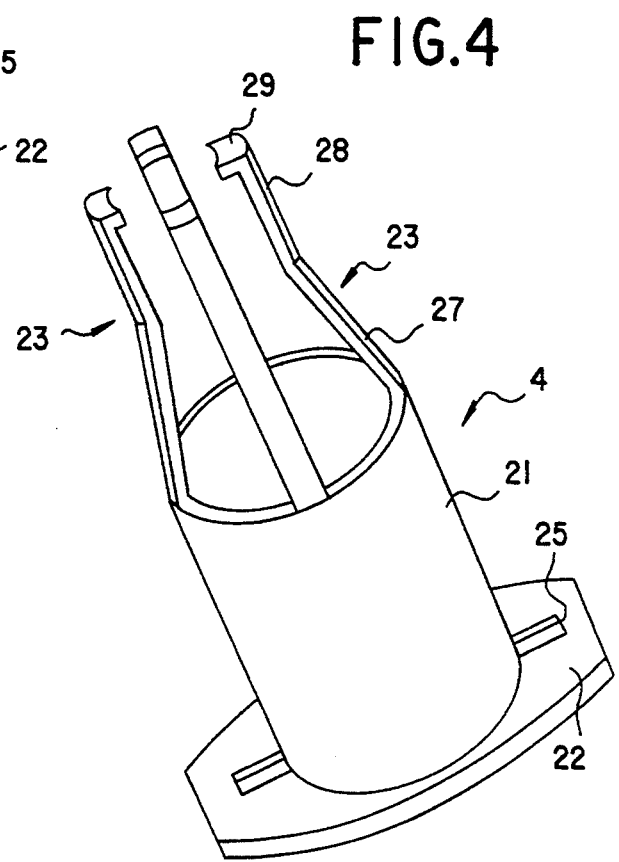
FIG. 4 is a perspective view showing the adapter in the first embodiment.

In FIGS. 1 to 3 showing a blood sampler in its entirety according to a first embodiment of the invention, the reference numeral 1 denotes a tube holder, the numerals 2 and 3 respectively denote a sampling needle and an evacuated blood sample tube, with the further numeral 4 indicating an adapter.

The tube holder 1 formed of a plastics such as polypropylene comprises a cylindrical body 5 of a given diameter, a conical end 6 forwardly protruding from the forward end of the body, and a flange 7 outwardly and radially extending from the rearward end of said body.

The sampling needle 2 secured to and through the conical end 6 comprises a hub 10 and a hollow needle body 11 penetrating the hub. The hub 10 is disposed at a middle region intermediate the open ends of needle body, and threaded to a central portion of the conical end 6 of the tube holder 1. An elastic sheath 12 made of an appropriate rubber fits on the needle body's rearward portion behind the hub 10 and has a forward end tightly adjoined thereto. Thus, the sheath does openably close the rearward opening of the needle body 11.

The blood sample tube 3, which is previously evacuated to be inserted in the tube holder 1 from its rearward open end, comprises a closed-bottom cylinder 14 having a forward open end closed with a plug 15. This plug is removably attached thereto. The cylinder 14 is made of glass or plastics, while the plug may be formed of either a rubber or be composed of a rubber core and a plastics cover tightly fitted thereon. A central zone 18 of the plug 15 is relatively thin in the direction of axis so as to be lightly pierced by the needle. In contrast with the central zone, a peripheral zone 19 of the plug is thick enough for the plug to be securely held by the cylinder 14.

The aforementioned adapter 4, which is removably inserted in the tube holder 1, intervenes between the holder and the evacuated tube 3. The adapter 4 is made of a flexible plastics such as polypropylene, polyethylene, polyvinyl chloride, polycarbonate, polystyrol or the like, and comprises a rearward main cylindrical body 21, a flange 22 and a plurality of forward flexible extensions 23. The main cylindrical body 21 has a diameter substantially uniform over its full length, with the flange 22 protruding radially outwards from the rearward end of said body. The number of the extensions 23 is four in this embodiment, and they are disposed at regular angular intervals around the forward end of the rearward main body 21.

This main body 21 of the adapter is tightly fittable in the cylindrical body of the tube holder 1. Lugs 25 formed on the flange 22 and bearing against the flange 7 in the axial direction will determine the deepest position of the inserted adapter 4 in the holder 1.

The forward flexible extensions 23 integral with the cylindrical body 21 protrude forwardly from and axially of the forward end of the main body 21 towards the forward tip end of the needle 2. Thus, the extensions will tightly surround the plug 15 of the inserted blood sample tube 3. Each flexible extension 23 comprises a rearward slanted portion 27 and a forward gripping portion 28 integral with and extending forwardly from the slanted portion. The slanted portion 27 of each extension 23 is inclined inwardly towards its forward end, so that this portion will be caused by the plug 15 to elastically swing outwardly when the tube 3 is inserted. The forward gripping portions 28 each have at their forward ends a protrusion 29 extending inwardly from there, are also capable of flexing following the swung rearward portions 27. Therefore, the gripping portions 28 will be transitionally displaced centrifugally and then restored to their straight position to hold the plug 15 in place.

Example 1 of the embodiment is a case wherein the plug 15 of the evacuated tube 3 for taking a blood sample has an outer diameter considerably smaller than the inner diameter of the tube holder 1, which constitutes the blood sampler as described above. The adapter 4 has to be set in the holder 1 at first as shown in FIG. 1, and then the sampling needle 2 is caused to pierce a vein. In this state, the rearward opening of the needle 2 is closed with the elastic sheath 12, so that there is no possibility that the blood leaks into said holder 1 to stain it, the tube 3 or the adapter 4.

Next, the evacuated blood sample tube 3 shall be forced into the adapter 4, with the tube's plug 15 in the lead.

The flexible extensions 23 around the plug 15 regulate the tube 3 to maintain its position coaxial with the holder and the adapter 4. Such a guiding action continues during the plug's forward movement to compress the elastic sheath 12. The rearward end of the needle 2 thus penetrating said sheath and the needle 2 does not pierce the peripheral zone 19 of plug 15 but exactly pierces its central zone 18.

The recent automatic blood analyzers widely employed necessitate an improved blood sample tube which is easier to be pierced by a sampling needle. Example 2 of the embodiment shown in FIG. 3 is designed to meet such a demand, wherein the central zone of the rubber plug 15 has a thickness of 1-2.5 mm in the direction of the axis of the evacuated tube 3. This blood sampler is used in a manner similar to Example 1. The needle 2 of the tube holder in which the adapter 4 is already inserted will be caused to pierce the vein, before the tube is forced into the adapter, also with the plug 15 in the lead.

The flexible extensions 23 surrounding the tube's plug 15 guide it while elastically flexing radially outwardly so that the plug can enter a space surrounded by the gripping portions 28 and be positioned coaxial with the adapter 4 and thus coaxial also with the tube holder 1. Since the gripping portions 28 were slanted outwardly towards their forward ends and exert a restoring forward moment to the tube's plug 15 which was being inserted, the backward force charged by the compressed elastic sheath to the tube 3 was observed not to "kick back" the plug to remove the needle 2 therefrom.

Reference 1 as a comparative example employed such a tube 3 as in Example 2, but without any adapter 4. It was observed that the axially compressed elastic sheath 12 caused the "kickback" phenomenon wherein the evacuated blood sample tube 3 was repelled backwards thereby withdrawing the needle 2 out of the plug 15.

Also in Example 2, the retaining action of the extensions 23 is realized in the same as in Example 1 to avoid the "kickback" phenomenon.

It will be understood that if the axial length of central zone 18 of the plug 15 and its diameter is so great as in the conventional blood sample tubes 3, the adapter 4 can be dispensed with so that only the tube is received in the holder 1 in order to take a blood sample. However, an adapter 4 similar to Examples 1 and 2 can be used also in that case, though the tube may encounter a stronger resistance when it is inserted with its plug being pierced by the needle, due to an increased friction between the large plug 15 and the flexible extensions 23 of adapter 4. This difficulty may be diminished easily by applying a silicone lubricant or the like to the whole inner surface of said adapter, as will be demonstrated below.

Second Embodiment

Figure 5:
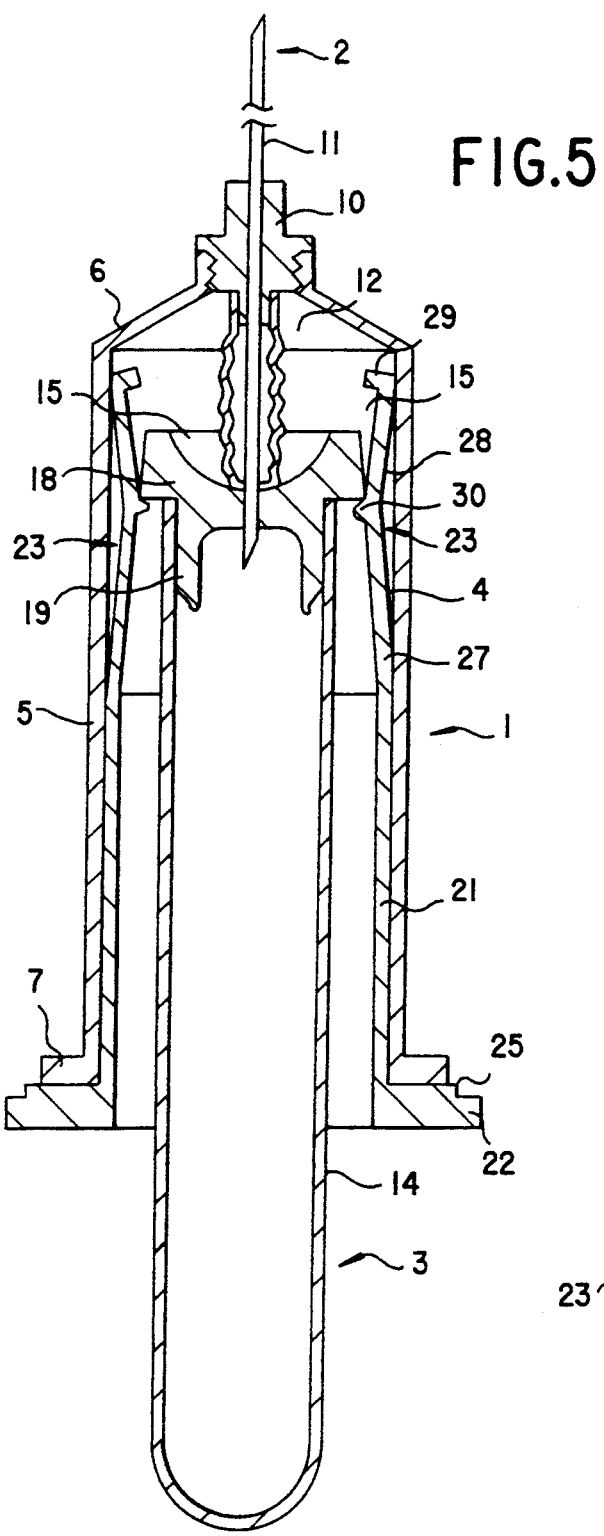
FIG. 5 is a further vertical cross section corresponding to FIG. 3 and showing a second embodiment of the invention, wherein a tube holder and an evacuated blood sample tube are illustrated together with an adapter.
Figure 6:
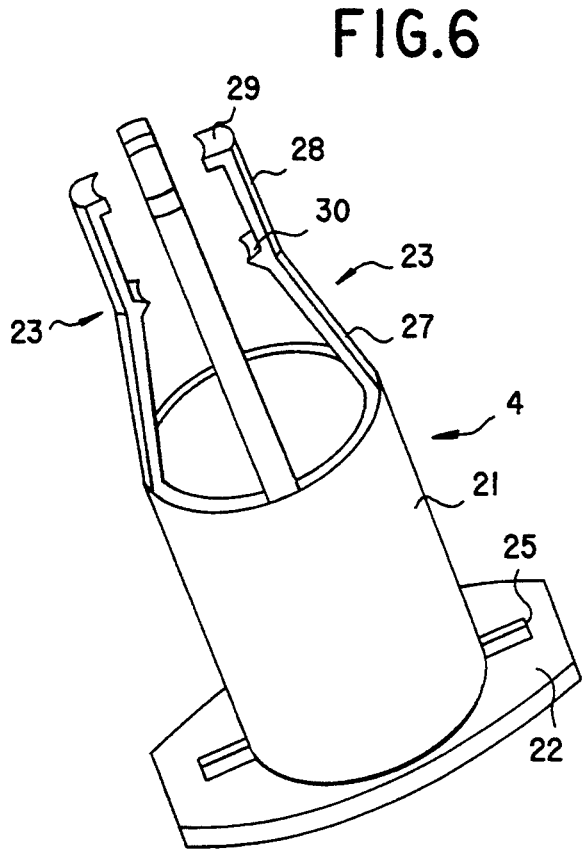
FIG. 6 is a perspective view showing the adapter in the second embodiment.

The important difference between the first and second embodiments resides in that a stopping lug 30, which is generally called an "undercut" in the molding of plastics, is formed integral with the rearward end of each gripping portion 28 as shown in FIGS. 5 and 6. The stopping lugs 30 disposed at the rearward ends of the gripping portions 28 prevent the plug 15 of the tube 3 from being unintentionally repelled out of the portions 28. The resistance against the insertion of the tube may be reduced in the second embodiment by decreasing the width of the extensions 23 or by forming the adapter from a slicker resin, provided that the stopping lugs are formed on the gripping portions, without a fear that the adapter could not be used many times.

Such an effect of the stopping lugs 30 will become more apparent from the Examples and References given below.

An overall resistance which the blood sample tube comprising the plug and the closed-bottom cylinder will encounter when inserted into the holder having the adapter previously set in place and the sampling needle covered with the elastic sheath, is a sum of components. One component is the friction between the inner periphery of adapter and the outer periphery of the tube's plug, while the other component is the resistance of said sheath and plug against the needle piercing them. The overall resistance was measured using an "Autograph" made by the Shimazu Seisakusho Co., Ltd.

A result of this measurement is given below for Examples 3 to 6 (including the first and second embodiments) and for References 2 and 3, in TABLE 1.

Instead of simply fitting the adapter in the tube holder either of the mating cylindrical bodies of tube holder and adapter may be formed with an annular groove which fits on an annular protrusion formed on the other cylindrical body so that said adapter can be more rigidly fixed in the holder. Alternatively, the adapter may be threaded in or adjoined to the holder by means of an adhesive.

In summary, the adapter provided herein is effective to position the tube's plug to be coaxial with the tube holder, thereby enabling the sampling needle to exactly pierce the central zone of the plug. Therefore, the adapter now eliminates the problem that the plug which has been fitted

TABLE 1

Evaluation Data

| EXAMPLES/REFERENCES | Extensions of Adapter | | | Plug | | | Overall resistance | "Kickback" |
|---|---|---|---|---|---|---|---|---|
| | Mat. | T(mm) | W(mm) | Mat. | Φ(mm) | T*(mm) | | |
| 1st EMBODIMENT | | | | | | | | |
| Example 3 | "PS" | 0.8 | 5 | butyl | | | | |
| Ex. 3-(1) | | | | | 17 | 6 | 2.0 Kgf | No |
| Ex. 3-(2) | | | | | 15 | 6 | 1.7 Kgf | No |
| Ex. 3-(3) | | | | | 17 | 2 | 1.2 Kgf | No |
| Example 4 | (the same extensions and plug as Ex. 3, but the extensions coated with a silicone) | | | | | | | |
| Ex. 4-(1) | | | | | 17 | 6 | 1.6 Kgf | No |
| Ex. 4-(2) | | | | | 15 | 6 | 1.6 Kgf | No |
| Ex. 4-(3) | | | | | 17 | 2 | 0.6 Kgf | No |
| Reference 2 | (the same as Ex. 3 but lacking the adapter) | | | | | | | |
| Ref. 2-(1) | | | | | 17 | 6 | 1.6 Kgf | No |
| Ref. 2-(2) | | | | | 15 | 6 | 1.6 Kgf | No |
| Ref. 2-(3) | | | | | 17 | 2 | 0.5 Kgf | Occurred |
| 2nd EMBODIMENT | | | | | | | | |
| Example 5 | "PP" | 0.8 | 3 | butyl | | | | |
| Ex. 5-(1) | | | | | 17 | 6 | 1.5 Kgf | No |
| Ex. 5-(2) | | | | | 15 | 6 | 1.5 Kgf | No |
| Ex. 5-(3) | | | | | 15 | 2 | 0.8 Kgf | Occurred (3rd ff.) |
| Example 6 | (the same extensions and plug as Ex. 5, but the extensions formed with stopping lugs) | | | | | | | |
| Ex. 6-(1) | | | | | 17 | 6 | 1.6 Kgf | No |
| Ex. 6-(2) | | | | | 15 | 6 | 1.5 Kgf | No |
| Ex. 6-(3) | | | | | 17 | 2 | 0.9 Kgf | No |
| Reference 3 | (the same as Ex. 5 but lacking the adapter) | | | | | | | |
| Ref. 3-(1) | | | | | 17 | 6 | 1.7 Kgf | No |
| Ref. 3-(2) | | | | | 15 | 6 | 1.6 Kgf | No |
| Ref. 3-(3) | | | | | 17 | 2 | 1.0 Kgf | Occurred (8th ff.) |

Notes:
'Mat.' = material, 'butyl' = butyl rubber, 'T' = thickness, * = central zone, 'W' = width, Φ = outer diameter, PS = polystyrol, PP = polypropylene. 10 tubes were tested for each adapter comprising four extensions.

in the tube's open end with a weaker friction and been pierced at its thicker peripheral zone by the needle against a stronger resistance would unintentionally be pulled off the tube's open end together with the needle.

Further, even the tube having its central zone extremely thin in axial direction is not "kicked back" but can be retained in position due to the action of the flexible extensions of the adapter and the stopping lugs which may be formed on said extensions. Thus, the extensions can be made relatively narrow and thin, and the adapter can be made of any appropriate resin. Therefore, even the conventional large-diameter tube having a thick central zone can be received smooth in the adapter to take a blood sample, and as lightly as is for conventional ones, if the adapter's inner surface is coated with a silicone or the like.

What is claimed is:

1. An adapter to be used with a blood sampler, the blood sampler including a tube holder, a double ended sampling needle having a first end extending through a top end of the holder, an elastic sheath fitted on and covering a second end of the double ended needle, an evacuated blood sample tube having a plug fitted in an open end of the tube, with the evacuated tube being adapted for insertion in a cylindrical body of the holder when a blood sample is to be taken, wherein during taking of a blood sample the elastic sheath is compressed in an axial direction so that the second end of the needle penetrates both the sheath and the plug so as to allow the blood sample to be sucked into the tube, the adapter being interposed between the holder and the evacuated blood sample tube, the adapter comprising:
   a cylindrical body having a circumferential outer dimension less than an inner dimension of the holder;
   a plurality of flexible extensions integral with and protruding from a top end of the cylindrical body;
   said flexible extensions extending axially of said body so as to surround the plug of an inserted blood sample tube;
   each of said flexible extensions comprising:
   a slanted portion inclined from the top end of the cylindrical body towards an axial center of the cylindrical body in a direction of the top end of the holder; and
   a gripping portion integral with the slanted portion and extending parallel to the axial center of the cylindrical body, said plug having a top portion with an outside diameter greater than an outside diameter of said evacuated tube, said top portion being in frictional contact with said gripping portion when the needle penetrates the plug, said frictional contact preventing movement of the tube in a direction away from said top end.

2. An adapter as defined in claim 1, wherein the number of extensions is three or more, and the extensions are arranged at regular angular intervals around the cylindrical body of the adapter.

3. An adapter as defined in claim 2, wherein the adapter has its inner surface coated with a silicone agent or the like as a lubricant.

4. An adapter as defined in claim 1, wherein each extension further comprises a stopping lug integral with and protruding inwardly from the gripping portion such that the tube's plug held thereby is prevented from slipping off the gripping portions.

5. An adapter as defined in claim 4, wherein the number of the forward flexible extensions is three or more, and the extensions are disposed at regular angular intervals around the cylindrical body of the adapter, and have a width of 3 mm or less.

6. A blood sampler comprising:
a tube holder,
a double ended sampling needle having a first end extending through top end of the holder, an elastic sheath fitted on and covering a second end of the needle,
an evacuated blood sample tube provided with an open end and a plug inserted therein the evacuated tube being adapted for insertion in the holder when a blood sample is to be taken, wherein during taking of the blood sample the elastic sheath is compressed in an axial direction so that the second end of the needle penetrates both the sheath and the plug so as to allow the blood sample to be sucked into the tube,
an adapter interposed between the holder and the evacuated blood sample tube, wherein the adapter comprises:
a cylindrical body having an outer dimension less than the inner dimension of the holder;
a plurality of flexible extensions integral with and protruding from a top end of the cylindrical body wherein the extensions extend axially of said body so as to surround the plug of an inserted blood sample tube, and wherein each of the flexible extensions has a slanted portion and a gripping portion, said gripping portion integral with and extending from the slanted portion toward said top end of said cylindrical body, the slanted portion is inclined radially inwardly from the top end of said cylindrical body towards a central axis of said cylindrical body in a direction of the top end of the holder, and the gripping portion extends from the slanted portion parallel to the central axis of said cylindrical body, said slanted portion frictionally engaging said plug so as to prevent movement of the tube in a direction away from said second end of the needle.

7. A blood sampler as defined in claim 6, wherein each extension further comprises a stopping lug integral with and protruding inwardly from the gripping portion such that the tube's plug held thereby is prevented from slipping off the gripping portions.

* * * * *